(12) United States Patent
Le Penske

(10) Patent No.: US 9,078,723 B1
(45) Date of Patent: Jul. 14, 2015

(54) DENTAL ORAL SHIELD DEVICE AND SYSTEM

(71) Applicant: ARMOR DENTAL CORP., Hingham, MA (US)

(72) Inventor: Cherie Le Penske, Hingham, MA (US)

(73) Assignee: ARMOR DENTAL, CORP., Hingham, MA (US)

( * ) Notice: Subject to any disclaimer, the term of this patent is extended or adjusted under 35 U.S.C. 154(b) by 0 days.

(21) Appl. No.: 14/137,188

(22) Filed: Dec. 20, 2013

(51) Int. Cl.
*A61C 5/14* (2006.01)
*A61C 5/12* (2006.01)

(52) U.S. Cl.
CPC .... *A61C 5/12* (2013.01); *A61C 5/14* (2013.01)

(58) Field of Classification Search
CPC ........................................................ A61C 5/15
USPC ........... 433/136, 93, 114, 116, 130, 139, 140, 433/146, 147, 162, 163
See application file for complete search history.

(56) References Cited

U.S. PATENT DOCUMENTS

| | | | | |
|---|---|---|---|---|
| 2,588,169 A | * | 3/1952 | Shea | 433/214 |
| 2,680,908 A | * | 6/1954 | Daigle | 433/136 |
| 3,974,567 A | | 8/1976 | Ridgeway | |
| 4,112,934 A | * | 9/1978 | Rizk | 600/210 |
| 4,671,260 A | * | 6/1987 | Buckner | 606/204.15 |
| 4,829,621 A | * | 5/1989 | Phenegar | 15/172 |
| 4,906,190 A | | 3/1990 | Michna | |
| 4,972,542 A | * | 11/1990 | Moshos et al. | 15/167.2 |
| 5,347,996 A | * | 9/1994 | Huan | 600/238 |
| 5,407,353 A | * | 4/1995 | Clementz | 433/93 |
| 5,490,780 A | * | 2/1996 | Riewenherm | 433/93 |
| 5,511,565 A | | 4/1996 | Syers | |
| 5,890,899 A | | 4/1999 | Sclafani | |
| 6,818,801 B2 | | 11/2004 | Ashman | |
| 7,331,788 B2 | * | 2/2008 | Kilcher et al. | 433/136 |
| 8,398,714 B2 | | 3/2013 | Boiangiu et al. | |
| 2001/0034474 A1 | * | 10/2001 | Ryan | 600/240 |
| 2004/0259055 A1 | | 12/2004 | Sherry et al. | |
| 2009/0029313 A1 | | 1/2009 | Chou | |
| 2012/0251978 A1 | | 10/2012 | Katz | |
| 2013/0065199 A1 | | 3/2013 | Morehead | |
| 2013/0068236 A1 | * | 3/2013 | Lovat | 128/862 |

FOREIGN PATENT DOCUMENTS

| | | |
|---|---|---|
| DE | 850333 C | 9/1952 |
| DE | 4434156 A1 | 3/1996 |
| EP | 0442855 A1 | 8/1991 |
| EP | 0442855 B1 | 3/1994 |
| TW | 201043201 A | 12/2010 |
| WO | WO-2007061411 A2 | 5/2007 |
| WO | WO-2009100525 A1 | 8/2009 |
| WO | WO-2009118725 A1 | 10/2009 |
| WO | WO-2013001530 A1 | 1/2013 |

OTHER PUBLICATIONS

International Search Report and Written Opinion in PCT/US2014/071444 dated Mar. 23, 2015 12 pages.

* cited by examiner

*Primary Examiner* — Ralph Lewis
(74) *Attorney, Agent, or Firm* — Goodwin Procter LLP

(57) ABSTRACT

An oral shield system for protecting an area in a patient's mouth, the system including an oral shield device having a molded body that forms a contoured surface and a pair of wings that extend from the body, and an elongate handle attached to the oral shield device.

28 Claims, 10 Drawing Sheets

DENTAL ORAL SHIELD DEVICE AND SYSTEM

FIELD OF THE INVENTION

Oral devices and systems for use after oral surgery and, more specifically, oral shields that help prevent dry socket, decrease pain during post-operative healing, and improve oral hygiene.

BACKGROUND OF THE INVENTION

Even the most successful and painless mouth surgery, e.g., tooth extractions, implants, bone grafts, hard tissue surgery, soft tissue surgery, gum surgery, and so forth, can be followed by days or weeks of discomfort for patients recovering from that surgery. Historically, patients are provided with a pain killer and some gauze pads and sent on their way to deal with their recovery. Between 5 and 8 percent of patients become afflicted with alveolar osteitis, i.e., "dry socket", and between 8 and 15 percent of patients develop a mild infection requiring another visit to the dentist's office. The problem centers around the need for continued oral hygiene, e.g., brushing and flossing one's teeth, in a post-surgical condition. Indeed, continued good oral hygiene decreases bacteria in the mouth, aiding the overall healing process and reduces the potential chances of swelling. In contrast, infrequent or no oral hygiene at all increases the likelihood of post-surgery infections. However, even when performing daily oral hygiene properly and carefully, contacting an area recently subjected to surgery or an extraction can be excruciatingly painful, if the toothbrush bristles or the toothbrush handle make contact with the area, which, as a result, reduces the chances the patient will keep up with hygiene following mouth surgery.

Consequently, there is a need for an oral device that acts as a barrier to protect the site of an implant, extraction, bone graft, and the like. More specifically, there is a need for such an oral barrier device that avoids inadvertent contact with the site during oral hygiene activity, e.g., brushing and flossing one's teeth.

SUMMARY OF THE INVENTION

In a first aspect, an oral shield device for protecting an area in a patient's mouth is disclosed. In various embodiments, the device is manufactured from at least one of a low durometer thermoplastic, a biocompatible material, silicone, fabric, a polymer, and any combination thereof.

In some embodiments, the device includes a molded body forming a contoured surface, e.g., concave, arcuate, arched, or hemispherical, and a pair of wings extending from the body. In one variation of the embodiment, during use, the contoured surface of the molded body is disposed on a lower surface of the body, proximate to the extraction area. Further, each wing of the pair of wings extends from the body proximate the contoured surface on the lower surface of the body. In another variation, the contoured surface forms an aperture through the body. In other variations, the pair of wings may be structured and arranged to oppose one another in use and each of the pair of wings may be substantially planar.

In another embodiment, the device further includes at least one detent or surface that is structured and arranged to be accommodated between adjacent teeth. In a variation of the embodiment, the at least one detent includes a pair of detents or surfaces and each detent of the pair of detents is adapted to releasably attach to a discrete tooth.

In other embodiments, the device may include an elongate handle having at a distal end thereof a connector that is structured and arranged to releasably attach to the molded body. In a variation of the embodiment, the connector forms an aperture adapted to mate with a projection disposed on the molded body or, alternatively, the connector includes a projection adapted to mate with an aperture formed on or in the molded body.

In a second aspect, an oral shield system for protecting an area in a patient's mouth is disclosed. In some embodiments, the oral shield system includes an oral shield device and an elongate handle having at a distal end thereof a connector attached to the device. The oral shield device may include a molded body forming a contoured surface, e.g., concave, arcuate, arched, or hemispherical, and a pair of wings extending from the body. In one variation of the embodiment, during use, the contoured surface of the molded body is disposed on a lower surface of the body, proximate to the extraction area. Further, each wing of the pair of wings extends from the body proximate the contoured surface on the lower surface of the body. In another variation, the contoured surface forms an aperture through the body. In other variations, the pair of wings may be structured and arranged to oppose one another in use and each of the pair of wings may be substantially planar.

In another embodiment, the device further includes at least one detent or surface that is structured and arranged to be accommodated between adjacent teeth. In a variation of the embodiment, the at least one detent includes a pair of detents.

In a variation of the embodiment, the connector forms an aperture adapted to mate with a projection disposed on the molded body or, alternatively, the connector comprises a projection adapted to mate with an aperture formed on the molded body.

In yet another embodiment, the elongate handle includes a flexible portion that can provide rotation and six degree of freedom. In one variation of some embodiments, the flexible portion can be rotated to provide a "gooseneck" orientation.

In a third aspect, a method of protecting an area in a patient's mouth is disclosed. In some embodiments, the method includes providing an oral shield device having a molded body forming a contoured surface and a pair of wings extending from the body and positioning the device over the area in the patient's mouth. In variations of the embodiment, providing an oral shield may include providing a molded body whose contoured surface is structured and arranged to retain the molded body at a distance from the area, so as not to contact the area.

BRIEF DESCRIPTION OF THE DRAWINGS

In the drawings, like reference characters generally refer to the same or similar parts throughout the different views. Also, the drawings are not necessarily to scale, emphasis instead generally being placed upon illustrating the principles of the invention. In the following description, various embodiments of the present invention are described with reference to the following schematic drawings, in which.

DETAILED DESCRIPTION OF THE INVENTION

Figure 1:
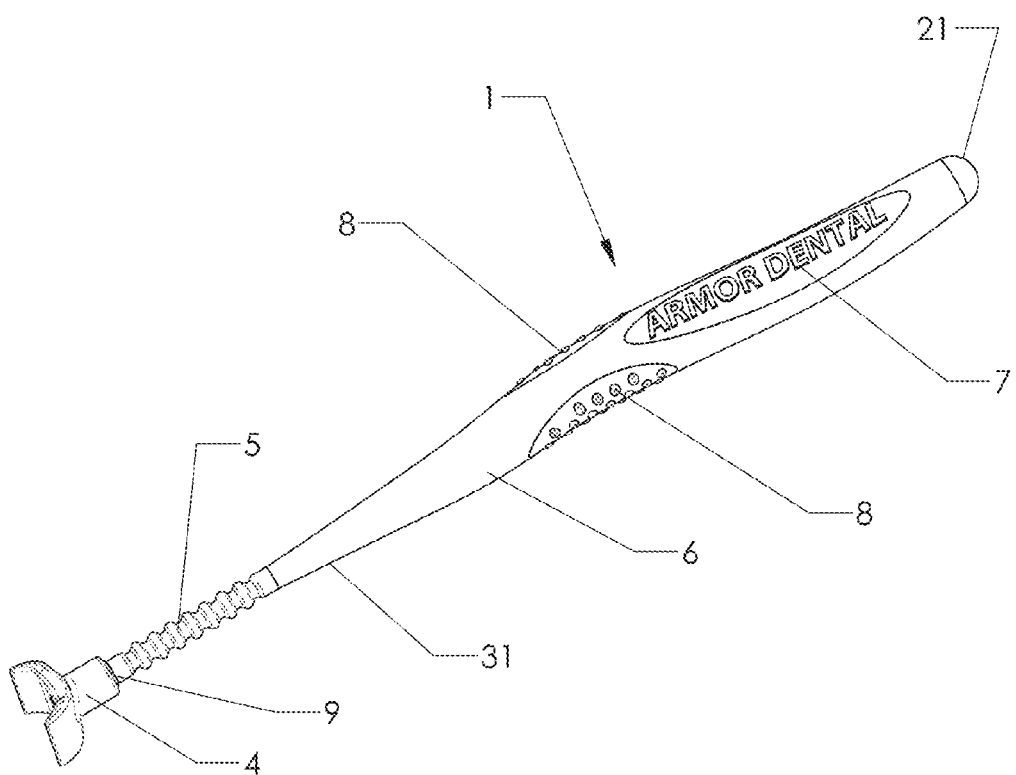
FIG. 1 depicts an isometric view of an embodiment of an oral shield system in accordance with the invention.
Figure 2:
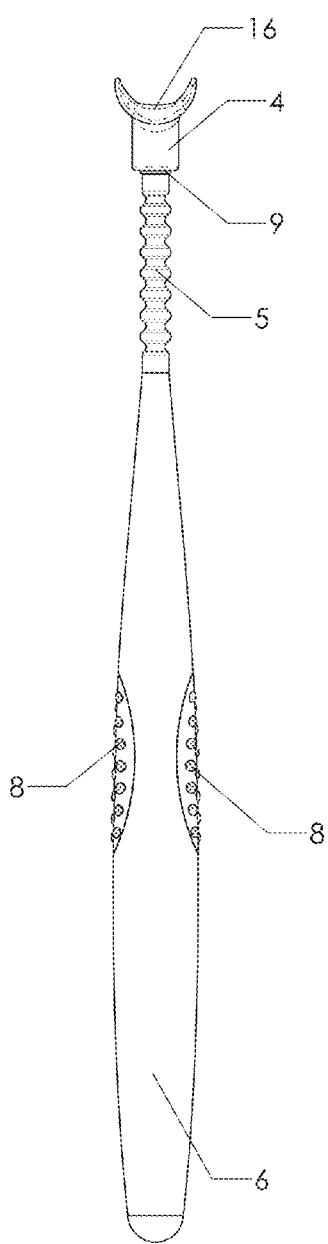
FIG. 2 depicts a rear elevation view of the embodiment of FIG. 1.
Figure 3:
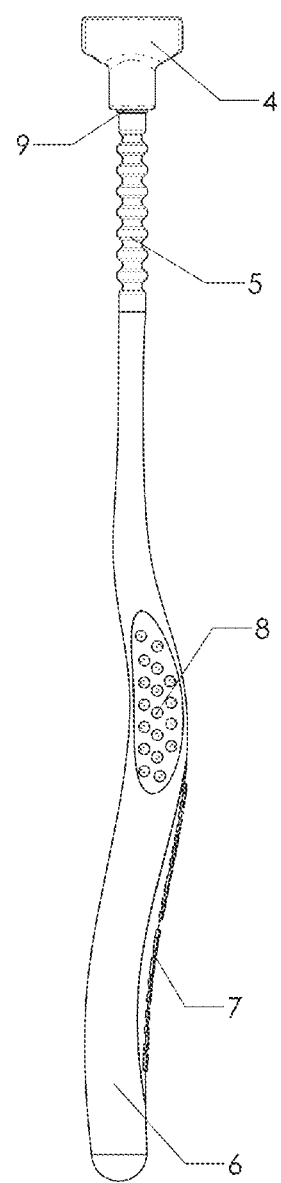
FIG. 3 depicts a side elevation view of the embodiment of FIG. 1.
Figure 4:
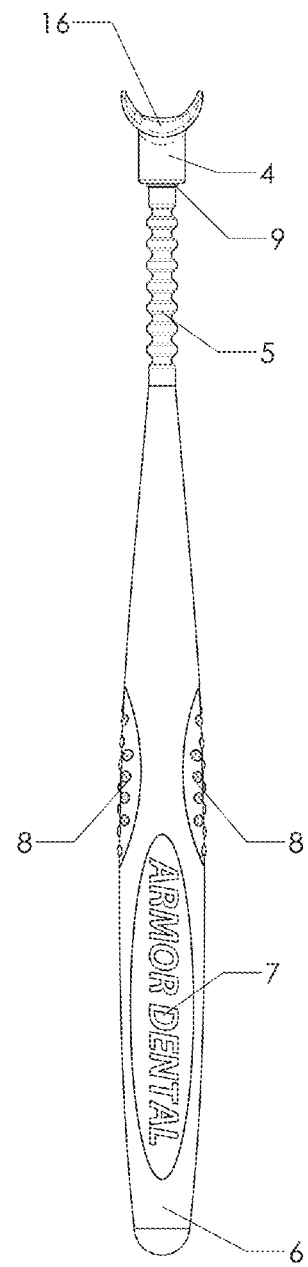
FIG. 4 depicts a front elevation view of the embodiment of FIG. 1.

Referring to FIGS. 1-4, an embodiment of an oral shield system 1 for post-surgical use is shown. This oral shield system 1 is structured and arranged to be used temporarily, e.g., during periodic, daily oral hygiene activity such as brushing and flossing. In some embodiments, the embodied system 1 may be configured to include an elongate handle 6 and an oral shield device 4.

The elongate handle 6 may be structured and arranged to include an elongate portion having a proximal end 21 and a distal end 31. The handle 6 may be shaped like a toothbrush handle and may be made of a material or materials that are flexible and bendable. Handle 6 may be cast or molded from a hard plastic, e.g., a high durometer thermoplastic, but also may include side grips 8 and/or a marque grip 7 to improve hand grip function for comfort and ease of use. For that purpose and to further improve gripping, side grips 8 and the marque grip 7 may be cast or molded from a low durometer thermoplastic. Optionally, for children, the handle 6 or the marque grip 7 may be cast in a smaller size and may include cartoon characters, favorite puppets, or comic book super heroes. Larger handles for older children and young adults can be cast as sports items, e.g., baseball bats, lacrosse sticks, hockey sticks and the like, and/or include a football, a soccer ball, a basketball, and the like.

Figure 5:
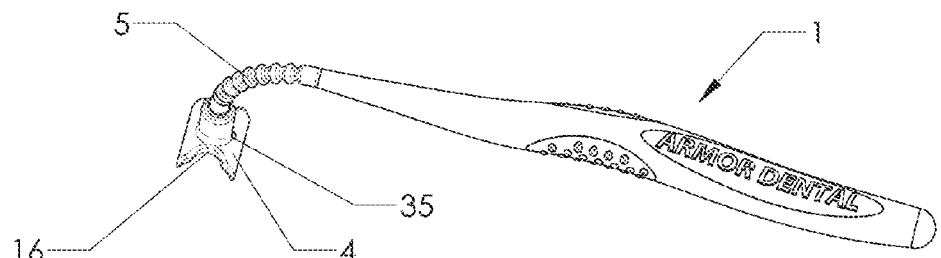
FIG. 5 depicts an isometric view of the embodiment of FIG. 1 in which a ductile wire and flexible cover are bent.
Figure 7:
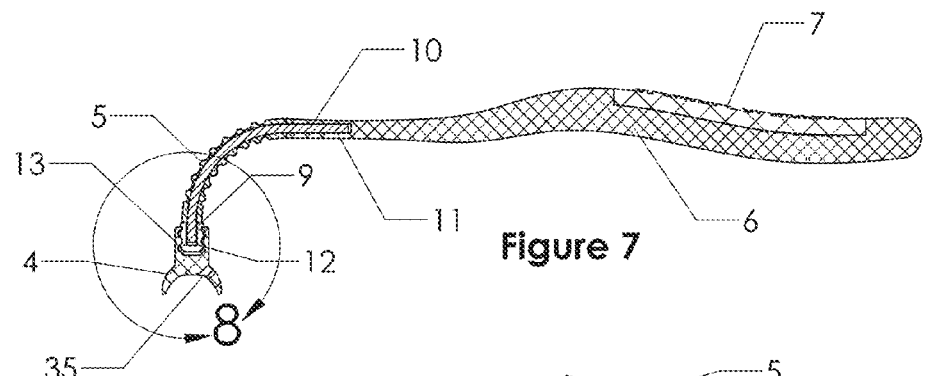
FIG. 7 depicts a cross-sectional side view of the oral shield system in which the ductile wire and flexible cover are bent as shown in FIG. 5.
Figure 12:
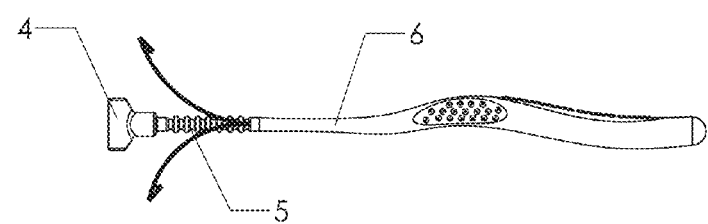
FIG. 12 shows a side elevation view of an elongate handle depicting a range of bending in accordance with one embodiment of the invention.
Figure 13:
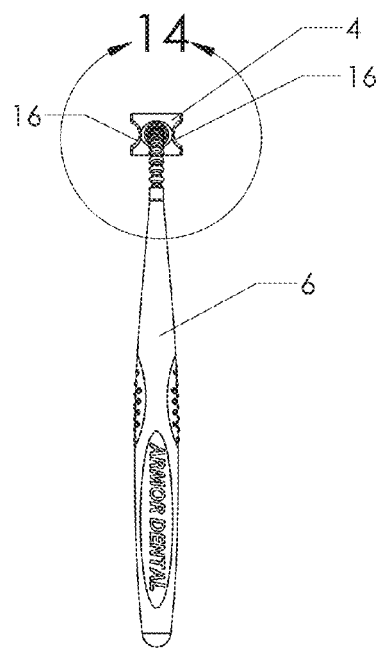
FIG. 13 depicts an illustrative embodiment of a pair of tooth detents formed in the oral shield device.
Figure 14:
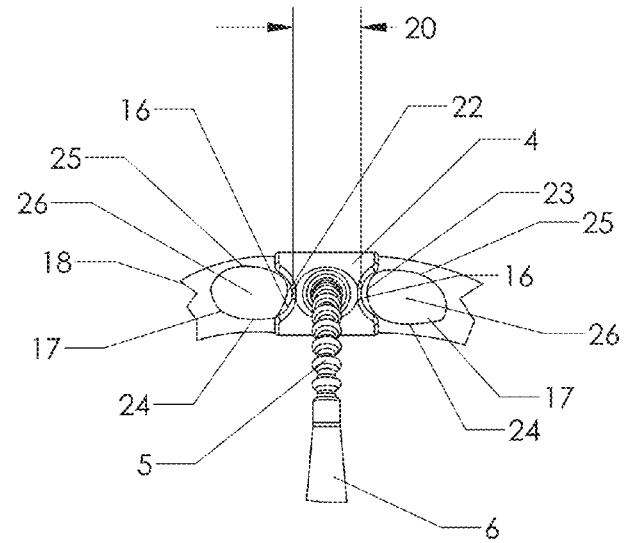
FIG. 14 depicts an embodiment of a method of inserting an oral shield device and the pair of tooth detents over an extraction site and between two adjacent teeth.

The distal end 31 of the handle 6 may be configured to include a flexible plastically deformable portion 5 and a shield retainer assembly 9. The shield retainer assembly 9 provides a mechanism for releasably connecting the elongate handle 6 to the oral shield device 4, e.g., to the flexible portion 5 of the oral shield device 4. The flexible portion 5 is structured and arranged to enable a user to vary the orientation, attitude, and distance of the oral shield device 4 relative to the handle 6. For example, as shown in FIGS. 5 and 7, by bending the flexible portion 5, the "pitch" of the flexible portion 5 of the elongate handle 6 may be adjusted. As shown in FIG. 12, the "yaw" of the elongate handle 5 may be adjusted, e.g., by bending the flexible portion 5. Pitch and yaw adjustments may range typically up to ±90 degrees or greater degrees from a nominal straight position. A particularly useful orientation for the flexible portion 5 provides a "gooseneck" appearance as shown, for example, in FIG. 7.

Figure 6:
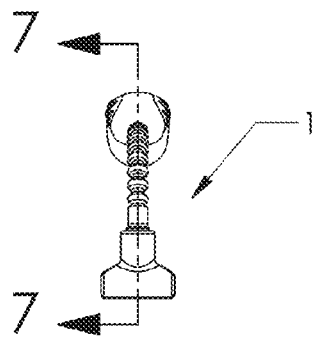
FIG. 6 depicts a detail of an embodiment of the molded body of the oral shield of FIG. 1.
Figure 8:
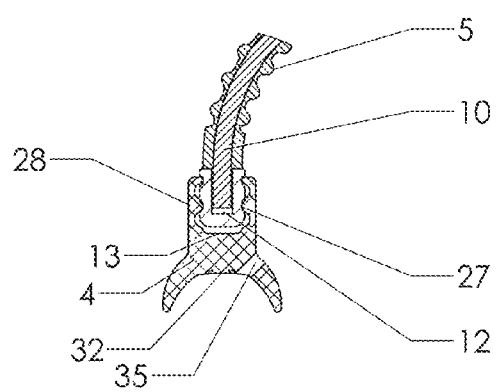
FIG. 8 depicts an enlarged detail view of the molded body and pair of wings of the oral shield device as shown in FIG. 7.

As shown in FIGS. 5 and 7, the flexible portion 5 at the distal end 31 of the elongate handle 6 may include an elongate, flexible, e.g., metal or alloy, rod or wire 10 that, at a first end, may be frictionally, e.g., with a tight, interference fit, or adhesively attached to the elongate handle 6, e.g., within an aperture 11 (FIG. 7) that is formed in the distal end 31 of the elongate handle 6. Alternatively, the handle 6 can be formed over an enlarged end of the wire 10, to provide positive retention. A flexible cover portion or sleeve (also labeled as 5) may be provided to cover the flexible wire or rod 10, e.g., to prevent contact with dental structures, to protect the flexible rod or wire 10 from water damage, and to improve the appearance of the system 1. Referring to FIGS. 6 and 8, the second end of the flexible rod or wire 10 may be frictionally, e.g., with a tight, interference fit, or adhesively attached to a shield retainer 9, e.g., within a retainer wire aperture 12. Alternatively, the retainer 9 can be formed over an enlarged end of the wire 10. As will be described in detail below, the shield retainer 9 is adapted to mate with the shield retainer socket 13 of the oral shield device 4 to releasably attach the oral shield device 4 to the handle 6. As a result, oral shield devices 4 may be readily changed or replaced and disposed of, without having to dispose of the elongate handle 6. Advantageously, the oral shield device 4 may be rotated about the axis of the flexible rod or wire 10 within the shield retainer 9 to allow a user to adjust the "roll" of the oral shield device 4, e.g., a full 360 degree rotation. Accordingly, the location and orientation of the oral shield device 4 in space is infinitely variable within the range of adjustment, providing six degree of freedom positioning of the oral shield device 4 relative to the handle 6, via rotation and/or translation of the flexible portion 5 in space.

Although the shield retainer assembly 9 shown in FIGS. 7 and 8 includes an end portion that is substantially cylindrical in shape, this is done for illustrative purposes only. Those of ordinary skill in the art can appreciate that the shape of the end portion of the shield retainer assembly 9 can assume practically any shape and the illustrated shape should not be interpreted as limiting the invention in any way. The illustrated embodiment of the end portion of the shield retainer assembly 9 includes a cylindrical or substantially cylindrical projection having at least one groove 27. The groove(s) 27 are structured and arranged to mate with one or more detent rings 28 that may be formed in the inner wall of the shield retainer socket 13 of the oral shield device 4.

Alternatively, in another embodiment, a retainer portion may be incorporated into the oral shield device 4 while a shield retainer socket may be incorporated at the distal end 31 of the elongate handle 6 such that the oral shield device 4 is retained within the shield retainer socket of the elongate handle 6 rather than vice versa. As above, a shield retainer socket incorporated into the elongate handle 6 may be structured and arranged to grab and releasably retain the retainer portion of the oral shield device 4. In yet another embodiment, the retainer portion and retainer socket interface can be positioned between the wire 10 and the handle 6. In all of these embodiments, any suitable mating interconnection can be employed, as long as the oral shield device 4 is reliably retained by the handle 6 during use and is not inadvertently released.

The oral shield device 4 may be designed of a material, as discussed below, that permits application over an extraction site in a patient's mouth for a longer period of time, e.g., hours, days, and so forth, before requiring removal. For longer term applications, an aperture 35 (FIG. 8) may be incorporated through the molded body 20, to enable air exchange with the extraction site 14, 15.

Referring to FIGS. 20-27, there are shown a variety of views of two embodiments of an oral shield device 4. The oral shield device 4 may be fabricated from an injection-molded plastic, e.g., a low durometer elastomer thermoplastic, another polymer, a fabric, silicone or any other single or composite material that is biocompatible and commonly used in the dental industry. A curvature of the contoured, bottom surface 32 of the oral shield device 4 may differ, depending on the particular application. Those skilled in the art may design the oral shield device 4 by selecting a radius of curvature and an arc length that are conducive to keeping the surface of the oral shield device 4 from contacting the protected area 14, 15. Furthermore, the molding of the contoured, bottom surface 32 of the oral shield device 4 may be configured to avoid hydrostatic adhesion to the gum surface. The dimensions of the oral shield device 4 may be varied to provide comfortable use for patients of various ages and to protect extraction sites of different sizes. The oral shield device 4 is typically disposable, but also may be immersed in an anti-microbial rinse, e.g., mouthwash, chlorhexidine rinse, and there reused.

The oral shield device 4 may be structured and arranged to include a molded body 20 and a pair of opposing wings or flaps 29. The molded body 20 may be configured to provide a contoured surface 32, e.g., a surface having a shape that is recessed, concave, arcuate, arched, hemispherical, and so forth, while the wings or flaps 29 may be similarly shaped or planar or substantially planar. For example, the contoured surface 32 of the molded body 20 may be provided on a lower surface of the molded body 20, which is the surface proximate an extraction or surgical area to be covered and protected, and the wings or flaps 29 may extend from the molded body 20 proximate the contoured surface 32 on the lower surface of the molded body 20. The molded body 20 may be adapted to include the shield retainer socket 13 described above. Optionally, the vent hole 35 or other aperture or relief may be provided through the molded body 20 of the oral shield device 4. One purpose of the vent hole 35 is to break any suction, i.e., negative pressure, that may form after application of the oral shield device 4. Another purpose of the vent hole 35 is to allow air into the affected area, e.g., to allow air exchange with the extraction site.

The wings or flaps 29 may be designed to extend downward from the molded body 20, generally away from the shield retainer socket 13. The wings or flaps 29 are structured and arranged to be applied to lingual and buccal sides of the gum adjacent the socket or affected area, i.e., the extraction site. The wings or flaps 29 are configured to oppose and may be biased toward one another in use. The length of the wings or flaps 29 should be long enough to completely cover the extraction site, e.g., on the buccal and lingual sides of the gums, to ensure that the bristles of a tooth brush do not disturb the underlying thrombus or cause undue pain or discomfort to the patient. For example, the length of each wing of flap measured from a tangent to the inside radius of the bottom of the contoured surface 32, typically, may be between 2 mm and 6 mm. However, in some applications, wing or flap lengths could be shorter than 2 mm and longer than 6 mm. In some variations of the embodiment, the contoured surface 32 forms an arched portion that is structured and arranged to minimize any contact between the molded body 20 of the oral shield device 4 and the affected area that it spans and covers. Thus, the wings or flaps 29—and hence the gums—support the oral shield device 4 and provide a snug fit.

Figure 20:
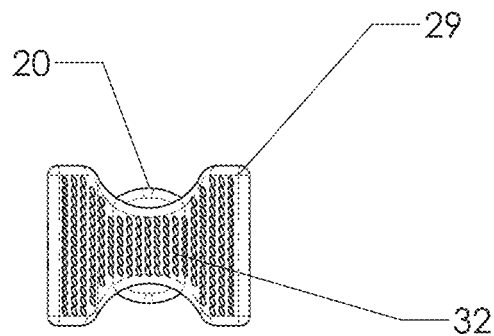
FIG. 20 depicts an illustrative bottom view of one embodiment of the contoured surface of the molded body and the pair of wings of an oral shield device for application at an extraction site between two adjacent teeth in accordance with the invention.
Figure 21:
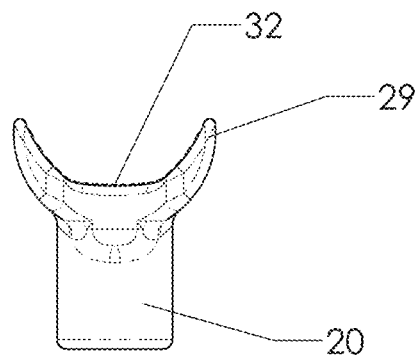
FIG. 21 depicts a side elevation view of an illustrative embodiment of the contoured surface of the molded body and the pair of wings of an oral shield device for application at an extraction site between two adjacent teeth in accordance with the invention.
Figure 22:
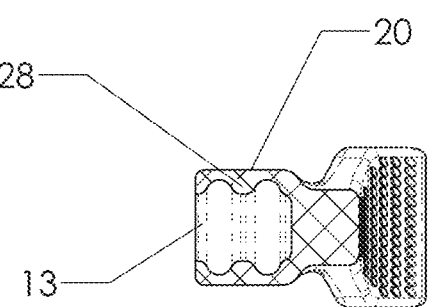
FIG. 22 depicts a top plan view of an illustrative embodiment of a retainer socket of an oral shield device for application at an extraction site between two adjacent teeth in accordance with the invention.
Figure 23:
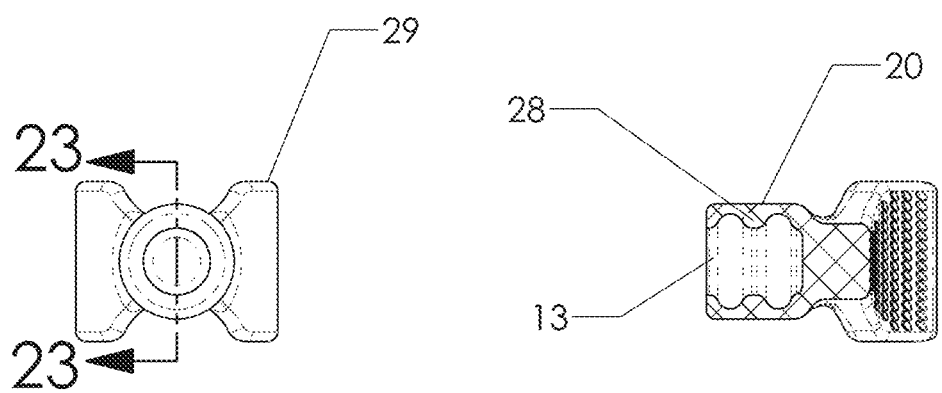
FIG. 23 depicts a cross-sectional side detail of an embodiment of a retainer socket of the oral shield device of FIG. 22 in accordance with the invention.
Figure 24:
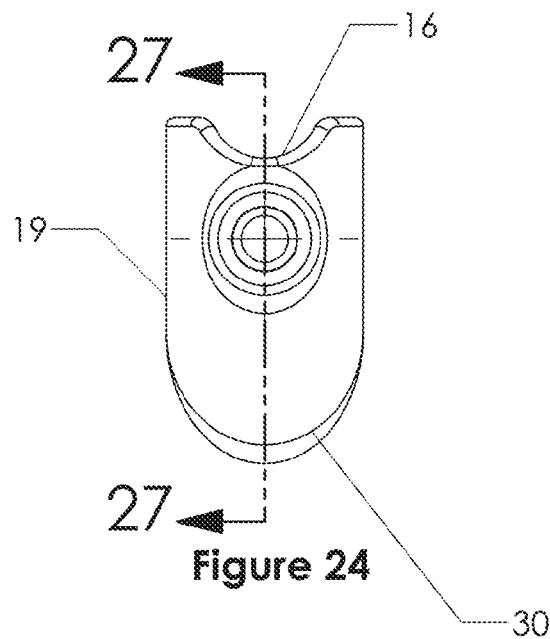
FIG. 24 depicts a top plan view of an illustrative embodiment of a retainer socket of an oral shield device for application at a wisdom tooth extraction site in accordance with the invention.
Figure 27:
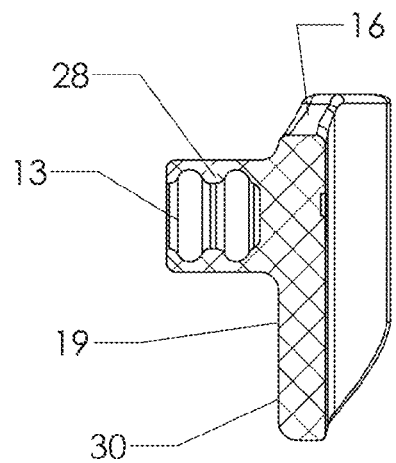
FIG. 27 depicts a cross-sectional side detail of an embodiment of a retainer socket of the oral shield device of FIG. 24 in accordance with the invention.
Figure 25:
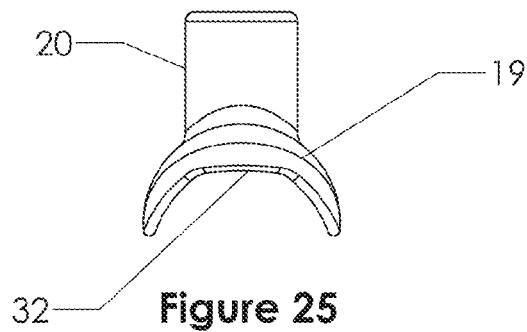
FIG. 25 depicts a side elevation view of an illustrative embodiment of the contoured surface of the molded body and the pair of wings of an oral shield device for application at a wisdom tooth extraction site in accordance with the invention.
Figure 26:
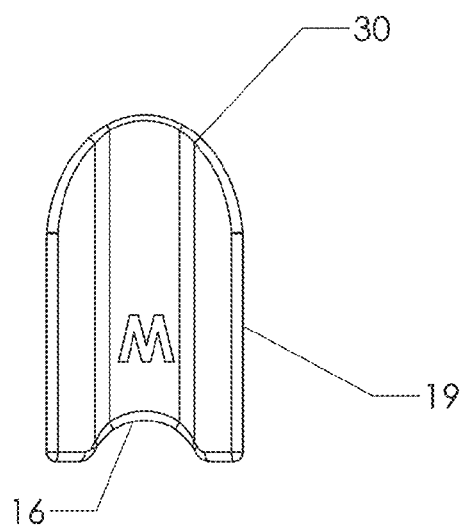
FIG. 26 depicts a bottom view of an illustrative embodiment of the contoured surface of the molded body and the pair of wings of an oral shield device for application at a wisdom tooth extraction site in accordance with the invention.

Texturing may be added to the contoured surface 32 to, inter alia, provide an irregular surface that reduces the total surface area in contact with the gingiva and that provides pressure relief channels. A standard commercial texture, e.g., MT-11260 manufactured by Mold-Tech, Inc. of Albertville, Minn., which includes a random pattern texture that is about 0.004 inches deep, may be used. However, those of ordinary skill in the art realize that any of a variety of commercially-available textures or custom textures can be added to or included with the contoured surface 32. Exemplary texturing to the contoured surface 32 is shown in FIGS. 20, 21, and 23.

Figure 9:
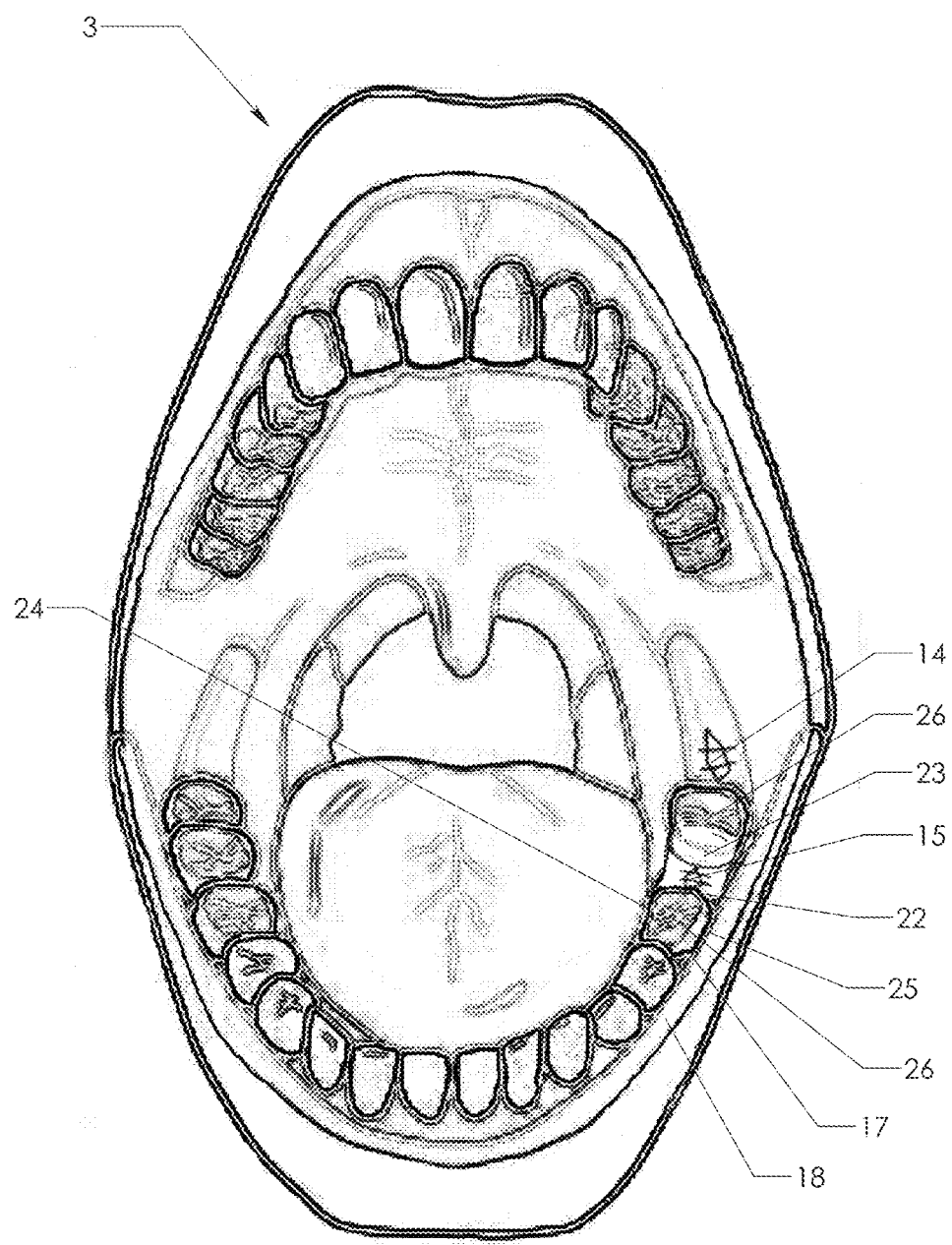
FIG. 9 shows an illustrative graphic of a human mouth depicting an extraction site and a wisdom tooth extraction site.
Figure 10:
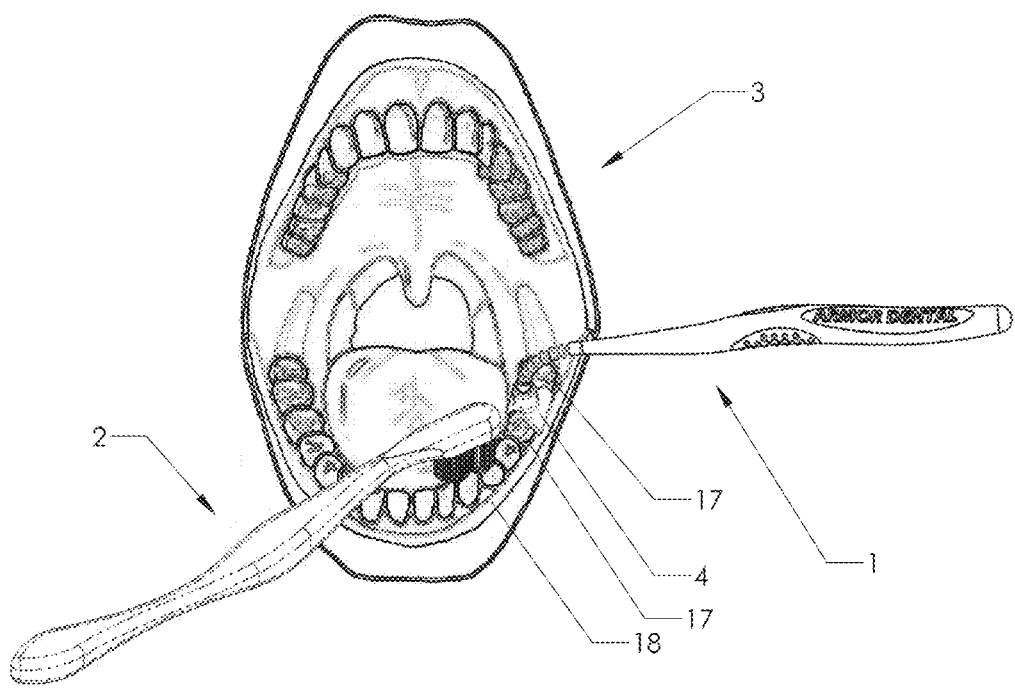
FIG. 10 depicts an embodiment of a method of using an embodiment of the oral shield device and system at an extraction site in accordance with the invention.
Figure 11:
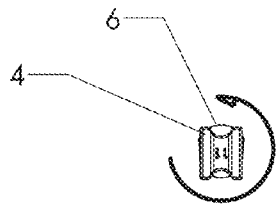
FIG. 11 depicts an end view of the oral shield device depicting a range of rotation in accordance with one embodiment of the invention.

The features of an oral shield device 4 may be modified for a specific application. For example, referring to FIG. 9, one application may be at a wisdom tooth extraction site 14 (FIG. 15) while another application may be at an extraction site 15 between two teeth 17 (FIG. 10). Typically gap ranges may be from about 4 to about 11 millimeters. FIGS. 13 and 14 and FIGS. 20-23, respectively, depict illustrative embodiments of an oral shield system 1 and an oral shield device 4 for use at an extraction site 15 between two teeth 17, while FIGS. 16-19 and FIGS. 24-27, respectively, depict illustrative embodiments of an oral shield system 1 and an oral shield device 4 for use at a wisdom tooth extraction site 14. For the former, a pair of tooth detents 16 may be provided on opposing sides of the molded body 20. As shown from the perspective of the occlusal 26 of a typical tooth 17, each tooth detent 16, which, for example, may be concave, arcuate, hemispherical, and so forth, is configured to accommodate a mesial 23 of a first tooth 17 and a distal 22 of a second tooth 17 on opposite sides of the extraction site 15.

For the wisdom tooth extraction shield 19 depicted in FIGS. 16-19 and 24-27, a single tooth detent 16 may be provided on one side of the molded body 20 opposed by an extended skirt 30 on the other side of the molded body 20. The tooth detent 16 may be concave, arcuate, hemispherical, and so forth, and is configured to accommodate a mesial of a last tooth before the extraction site 14. Because there is only one adjacent tooth, an extended, i.e., longer, skirt 30 is provided to enhance the stability of the shield placement and to protect a greater area.

Figure 15:
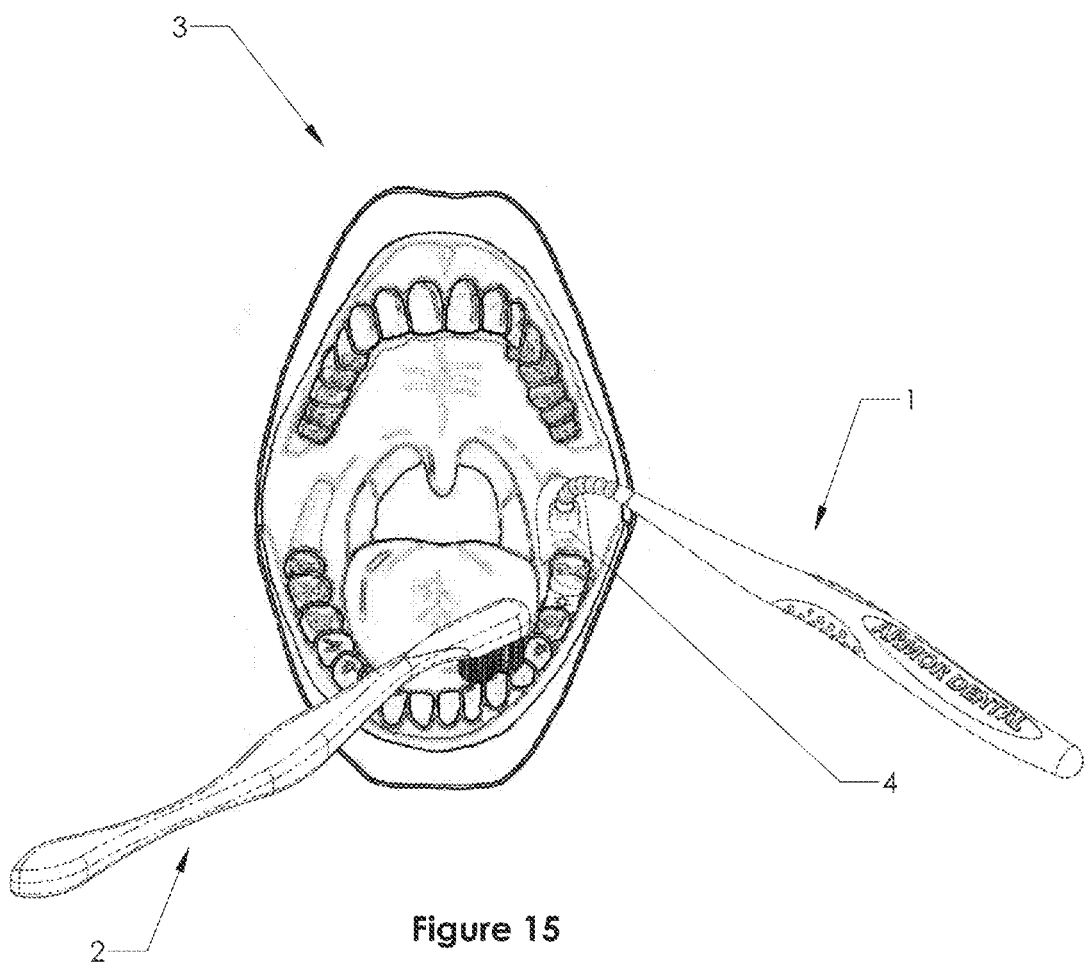
FIG. 15 depicts an embodiment of a method of using an oral shield device at a wisdom tooth extraction site in accordance with the invention.
Figure 16:
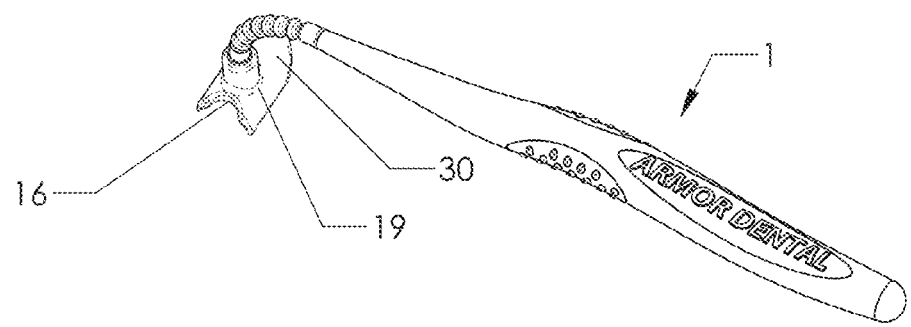
FIG. 16 depicts an isometric view of an embodiment of an oral shield system for a wisdom tooth extraction application in accordance with the invention.
Figure 17:
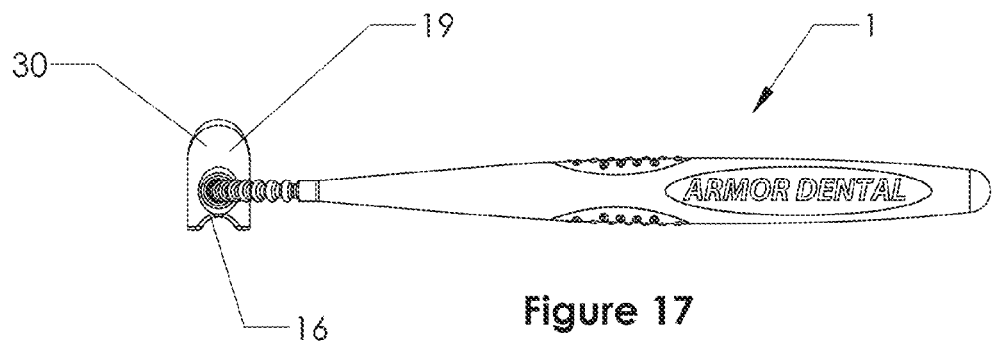
FIG. 17 depicts a front elevation view of an embodiment of an oral shield system for a wisdom tooth extraction application in accordance with the invention.
Figure 18:
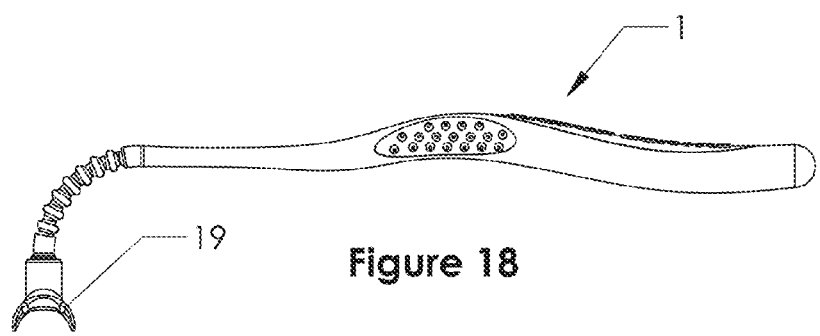
FIG. 18 depicts a side elevation view of an embodiment of an oral shield system for a wisdom tooth extraction application in accordance with the invention.
Figure 19:
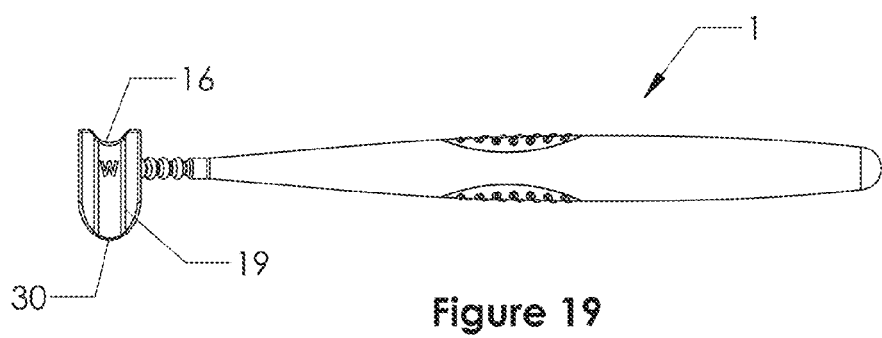
FIG. 19 depicts a rear elevation view of an embodiment of an oral shield system for a wisdom tooth extraction application in accordance with the invention.

Having described certain embodiments of the elongate handle 6 and oral shield device 4 of the oral shield system 1, a method of using the oral shield system 1, for example during performance of personal oral hygiene, is now described. FIG. 10 depicts an illustrative embodiment of use of the system 1 in combination with a toothbrush 2 when the extraction site 15 is between a pair of teeth 17. FIG. 15 depicts an illustrative embodiment of use of the system 1 in combination with a toothbrush 2 with a wisdom tooth extraction site 14. Prior to inserting the oral shield device 4 into her mouth 3, a user may bend or otherwise adjust the flexible portion 5 of the oral shield system 1 to facilitate positioning the oral shield device 4 where desired, i.e., proximate the extraction site 15 or the wisdom tooth extraction site 14.

Preferably, the user may center the molded body 20 and, more particularly, the contoured surface 32 so that the one of the opposing flaps or wings 29 is positioned on the lingual side of the user's gingiva (gums) 18 and the other of the opposing flaps or wings 29 is positioned on the buccal side of the user's gingiva 18. As the oral shield device 4 is lowered or raised into position as the case may be, each of the tooth detents 16 accommodates the distal 22 or mesial 23 of the adjacent teeth 17. The distance between the detents 16 and the contoured surface 32 of the molded body 20 are sized and configured to prevent the oral shield device 4 from contacting the thrombus or exposed bone, which would be the source of great discomfort and also may cause other complications. The wings of flaps 29 extend along the gingiva 18 to seal off the extraction site from the sides.

Once the extraction site 14 or 15 has been covered by the oral shield device 4, the user inserts her toothbrush 2 and begins to brush her teeth as she normally would. The wings or flaps 29 and the molded body 20 cover the extraction site 14 or 15, preventing the bristles of the tooth brush 2 from disturbing the healing process. This prevents discomfort or pain and avoids possibly infecting the extraction site 14 or 15.

The foregoing description of various embodiments of the invention has been provided for the purposes of illustration and description. It is not intended to be exhaustive or to limit the claimed subject matter to the precise forms disclosed. Many modifications and variations will be apparent to the practitioner skilled in the art.

For example, more or less of the handle may be plastically deformable, up to an entire length of the handle or none at all. In the latter case, the handle may include a substantially rigid gooseneck or other non-linear configuration. Alternatively or additionally, the shield retainer assembly may be a ball-and-socket or multi-axis swivel connection, allowing further adjustability of the oral shield device relative to the handle. In certain embodiments, the oral shield device may be manufactured integrally with the handle, eliminating the need for the shield retainer assembly. In other embodiments, once the oral shield device is attached to the handle with the shield retainer assembly, the combination may form an inseparable assembly.

Embodiments were chosen and described in order to best describe the principles of the invention and its practical application, thereby enabling others skilled in the relevant art to understand the claimed subject matter, the various embodiments and with various modifications that are suited to the particular use contemplated. All combinations and permutations of structures, methods, and materials disclosed herein are considered to be part of the invention, as well as all equivalents. The scope of the invention is to be defined by the following claims and not limited to any particular embodiment.

The invention claimed is:

1. An oral shield device for protecting an area in a patient's mouth, the device comprising:
   a compliant, molded body forming a contoured surface, the molded body having a closed-end socket adapted to receive and reliably retain therein an end of a handle about which, when in the patient's mouth, the molded body can rotate; and
   a pair of similarly shaped wings extending from the body a similar length and sized and configured to be applied over a buccal side and a lingual side of human gingiva adjacent the area to be protected such that a first wing is disposed only on the buccal side and a second wing is disposed only on the lingual side of the human gingiva.

2. The device of claim 1, wherein the contoured surface of the molded body is disposed on a lower surface of the body to be proximate to the area during use.

3. The device of claim 2, wherein the contoured surface is at least one of recessed, concave, arcuate, arched, and hemispherical.

4. The device of claim 2, wherein each wing of the pair of wings extends from the body proximate the contoured surface on the lower surface of the body.

5. The device of claim 1, wherein the contoured surface forms a vent aperture to permit solely air exchange with the area during use.

6. The device of claim 1, wherein the pair of wings is structured and arranged to oppose one another in use.

7. The device of claim 1, wherein each of the pair of wings is substantially planar.

8. The device of claim 1, wherein the device is manufactured from at least one of a low durometer thermoplastic, a biocompatible material, silicone, fabric, a polymer, and any combination thereof.

9. The device of claim 1 further comprising at least one detent structured and arranged to accommodate an adjacent tooth.

10. The device of claim 9, wherein the at least one detent includes at least one pair of detents and each detent of the pair of detents is adapted to accommodate a discrete tooth.

11. The device of claim 1 further comprising an elongate handle having at a distal end thereof a connector structured and arranged to attach to the molded body.

12. The device of claim 11, wherein the connector comprises a projection adapted to mate with the socket formed on the molded body.

13. An oral shield system for protecting an area in a patient's mouth, the shield system comprising:

a rotatable oral shield device including:
a molded body forming a contoured surface and a closed-end socket; and
a pair of wings extending from the body; and
an elongate handle having at a distal end thereof a connector mated with and reliably retained within the closed-end socket, the elongate handle including a bendable portion plastically deformable in multiple degrees of freedom, to enable repositioning the rotatable oral shield device relative to a grip portion of the handle, and having an axis about which the rotatable oral shield device may be rotated when in use in the patient's mouth.

14. The system of claim 13, wherein the contoured surface of the molded body is disposed on a lower surface of the body to be proximate to the area during use.

15. The system of claim 14, wherein the contoured surface is at least one of recessed, concave, arcuate, arched, and hemispherical.

16. The system of claim 14, wherein each wing of the pair of wings extends from the body proximate the contoured surface on the lower surface of the body.

17. The system of claim 13, wherein the bendable portion is plastically deformable to provide a gooseneck orientation.

18. The system of claim 13, wherein the oral shield device is manufactured from at least one of a low durometer thermoplastic, a biocompatible material, silicone, fabric, a polymer, and combinations thereof.

19. The system of claim 13, wherein the oral shield device further includes at least one detent structured and arranged to accommodate an adjacent tooth.

20. The system of claim 19, wherein the at least one detent includes at least one pair of detents and each detent of the pair of detents is adapted to accommodate a discrete tooth.

21. The system of claim 13, wherein the connector comprises a projection forming at least one groove mated with at least one ring formed in the socket.

22. A method of protecting an area in a patient's mouth, the method comprising:
providing a rotatable oral shield system including:
a molded body forming a contoured surface and a closed-end socket;
a pair of wings extending from the body; and
an elongate handle having at a distal end thereof a connector mated with and reliably retained within the closed-end socket, the elongate handle including a bendable portion plastically deformable in multiple degrees of freedom, to enable repositioning the rotatable oral shield device relative to a grip portion of the handle, and having an axis about which the rotatable oral shield device may be rotated when in use in the patient's mouth; and
positioning the device over the area in the patient's mouth with the handle.

23. The method of claim 22, wherein providing an oral shield includes providing a molded body contoured surface structured and arranged to retain the molded body at a distance from the area so as not to contact the area.

24. The method of claim 22 further comprising disposing each of the pair of wings on opposing sides of the area when positioning the device over the area.

25. The method of claim 22, wherein the device comprises at least one detent, the method further comprising releasably abutting the at least one detent to a tooth adjacent to the area.

26. The method of claim 25, wherein abutting the at least one detent to an adjacent tooth retains the molded body proximate the area so as not to contact the area.

27. The method of claim 22, wherein the pair of wings is similarly shaped and extends from the body a similar length and sized and configured to be applied over a buccal side and a lingual side of human gingiva adjacent the area to be protected.

28. The method of claim 22, wherein the handle includes a bendable portion plastically deformable in multiple degrees of freedom, to enable repositioning the oral shield device relative to a grip portion of the handle, and having an axis about which the oral shield device may be rotated.

* * * * *